(12) United States Patent
McElhaney et al.

(10) Patent No.: US 6,637,259 B2
(45) Date of Patent: Oct. 28, 2003

(54) PORTABLE GRAIN MOISTURE METER

(75) Inventors: Trent A. McElhaney, North Jackson, OH (US); James T. Falbo, Stow, OH (US); John W. Dubay, Chagrin Falls, OH (US)

(73) Assignee: Worens Group Inc., Sarasota, FL (US)

( * ) Notice: Subject to any disclaimer, the term of this patent is extended or adjusted under 35 U.S.C. 154(b) by 0 days.

(21) Appl. No.: 09/932,880

(22) Filed: Aug. 20, 2001

(65) Prior Publication Data

US 2003/0033862 A1 Feb. 20, 2003

(51) Int. Cl.[7] .......................... G01N 5/02; G01N 27/12; G01R 27/26
(52) U.S. Cl. .................. 73/73; 73/74; 324/644; 324/689; 324/694
(58) Field of Search ............... 73/73, 74, 1.01, 73/1.88; 324/644, 689, 694, 670, 664

(56) References Cited

U.S. PATENT DOCUMENTS

| | | | |
|---|---|---|---|
| 5,192,938 A | * 3/1993 | Ort | 338/5 |
| 5,493,229 A | * 2/1996 | Mc Mahon | 324/664 |
| 5,663,650 A | * 9/1997 | McMahon | 324/670 |
| 5,994,908 A | * 11/1999 | Mc Mahon | 324/694 |
| 6,088,657 A | * 7/2000 | McMahon | 702/50 |
| 6,340,892 B1 | * 1/2002 | Rynhart et al. | 324/640 |

* cited by examiner

Primary Examiner—Daniel S. Larkin
Assistant Examiner—K Wilson
(74) Attorney, Agent, or Firm—Vytas R. Matas

(57) ABSTRACT

A portable grain moisture measurement device automatically initiates testing at a predetermined grain compression and is calibrated to commercial moisture testers found in various commercial grain elevators so the user can select the commercial tester he wants to match moisture measurements with. The portable meter user can thus set the tester to match the commercial tester which will be testing his grain and can also perform calibration offset adjustments to further conform measurements between his meter and the particular commercial tester actually used, relative to the default moisture curves for each commercial tester, and each type of grain.

8 Claims, 4 Drawing Sheets

PORTABLE GRAIN MOISTURE METER

BACKGROUND OF THE INVENTION

1. Field of the Invention

The present invention relates generally to portable testers for measuring the water content of a material using a measurement of the dielectric constant of the material, and more particularly to such a moisture tester which uses lookup tables that are calibrated to match the moisture measurement ranges of several commercial moisture testers and which measurements allows offset calibration adjustments to more closely match individual commercial testers being used.

2. Description of the Prior Art

There have previously been portable grain moisture testers that have been calibrated to absolute grain moisture. One shortcoming of this is when the portable moisture tester measurement is taken in the field and is then compared to a commercial tester measurement at the grain purchase site and the two measurements do not give the same result. Since the farmer's return for selling his grain is directly correlated to the optimum percent moisture content as measured by the commercial tester, the portable unit needs to match the commercial tester and provide harvesting of the grain at this optimum commercial measurement. Prior art devices failed to overcome this mismatch and provided no way to calibrate the portable tester to several commercial testers instead of calibrating directly to absolute moisture.

Portable grain moisture testers are known and are described in U.S. Pat. Nos. 4,462,250 and 3,739,264. They give no option of selecting a grain moisture curve to match the commercial tester. Each of these units has one fixed moisture curve per grain. While this is a valid approach, it has been revealed that calibrating to several commercial testers, and allowing the user to select the calibration curve results in a more cost effective grain measurement which results in a top price for the grain at the commercial tester site by insuring an optimum moisture measurement with no penalties for drying overly wet grain.

Prior art portable moisture meters as shown in U.S. Pat. No. 5,663,650 teach a method for providing offset adjustments in an attempt too more closely match the commercial testers. These meters offer a single offset for the entire moisture span which eliminates the possibility of adjusting to the commercial tester's complete moisture span, and only allows the user to add a single calibration offset to the entire moisture curve. This method is acceptable if the user is always working in a narrow window of the total moisture span. However, the lack of multiple offsets over the entire grain moisture span would sometimes cause an adjusted low moisture range to match the elevator but the higher moisture would be further off than if it was with zero offset because low and high moisture offsets are often of opposite polarity.

Also, known prior art portable moisture meters provided compaction of the grain test sample by filling the test cell with grain and compressing it by screwing down the cap over the test cell. This provided a test under differing grain compactions depending on the strength or disposition of the person initiating the test resulting in a lack of complete repeatability of testing. There was no provision for initiating a test under a preset compaction of the grain sample.

In view of the forgoing it will be seen that the prior art portable grain moisture measurement devices failed to provide a repeatable test under a preset constant compaction or pressure, did not calibrate to several commercial moisture testers and did not provide sufficient calibration offset.

SUMMARY OF THE INVENTION

The present invention solves the problems associated with prior art portable moisture meters and others by providing a meter which has a means for a farmer to closely match the measurements of various commercial elevator testers for the commodity that he is selling to insure optimum moisture content measurements by the commercial tester. Since most testers calibrations are based on absolute moisture and every manufacture has a different calibration it is very difficult for a moisture tester with one calibration to match a large range of commercial testers on the market. The present device uses multiple calibrations, each commodity to be tested has a different calibration for each of the commercial testers that the farmer may encounter at his particular grain purchase site. This will ensure that the farmer can more closely match the site's elevator tester measurements for optimum moisture content.

To accomplish this end, the present device use a graphic LCD with a menu driven interface to not only allow the operator to select the commodity to be tested but also to select the commercial tester that his measurements will be compared against.

Before the farmer begins to test the commodity he first turn on the tester. The tester's LCD will display on the screen some instructions, and also the last commodity that was tested. Next he presses the menu button. The tester now displays a series of menu options the user will then using the arrow keys move the pointer down to select the menu option commercial tester and press the enter key. The tester now displays the list of commercial testers that are calibrated in the tester. Using the arrow keys he moves the pointer to the commercial tester that he wants to compare to and presses enter. Once enter is pressed the selection is stored and the tester returns to the main menu display. The farmer can now either select another menu option or press the cancel button to return to the main screen where the commodity to be tested is displayed. The user can now prepare to test that commodity or use the up down arrows to select a different commodity.

To initiate a test with the tester the user fills the tester with the commodity he wants to measure. Once the test cell is full the tester will display TEST INITIATED and the farmer now has 60 seconds to place the cap on the unit and tighten down the cap. The tester now, by measuring the compaction of the commodity in the cell, determines the correct time to take a test. This is done by having the test start automatically at a predetermined pressure on the grain sample in the cell as determined by a strain gauge located in the cell. The strain gauge signal is compared to a preset level stored in a microprocessor which initiates testing upon detecting the preset level. The pressure on the grain is done by screwing down the cap of the tester. Once the test is initiated the tester will audibly beep and provide an indication on the LCD showing TESTING. At this point the user should stop tightening the cap and the tester is now measuring the commodity to determine the moisture by measuring the dielectric of the commodity and also the temperature. Once it is done the tester uses the dielectric reading to lookup the corresponding moisture value using the calibration curve for the commercial tester selected by the user and then applies any user offset that have been made. The tester then applies the temperature compensation to the resulting moisture value based not only by the temperature of the commodity but also the initial moisture calculated before temperature compensation. Then the tester displays on the screen the current moisture value of the last six tests and the average of them.

If the user is not satisfied that his portable tester matches the commercial tester, he has the option of adjusting the calibration of his tester by pressing a cal button. After the cal button is pressed a menu appears giving him the option to reset or adjust the calibration of the tester. If he selects RESET all the offsets that were in the tester will be set back to factory calibration. A menu will appear to confirm that he wishes to reset the given commodity using the selected commercial tester. If the user wishes to adjust the moisture reading, a new window will appear showing the value of the current moisture tested and also showing the same value for the commercial tester. The user can now use the arrow keys to adjust the reading to the actual reading of the particular commercial tester he is selling his grain to by not just applying an offset but actually changing his tester reading to that of the commercial tester. The tester now shows on the display the amount of adjustment that the user has made as well as the maximum amount that he can adjust. Once the adjustment is made the tester takes the offset value and applies it to the calibration of the commodity only in the moisture range of the current test. The tester does not apply an offset to the whole calibration but only to the point that was just tested. This is important for reason as described above.

From the foregoing it will be seen that one aspect of the present invention is to provide a portable grain moisture meter having a stored memory of commercial tester moisture meter measurement ranges for numerous commercial tester manufacturers which may be used in the portable meter.

Another aspect of the present invention is to provide a portable grain moisture meter having a stored memory of commercial tester moisture meter measurement ranges for numerous commercial tester manufacturers which may be manually changed by the portable meter user to conform a stored measurement to an actual measurement of a particular commercial tester.

Still yet another aspect of the present invention is to provide a portable grain moisture meter having an automatic test initiation of moisture measurement upon a predetermined test cell compaction of grain therein.

These and other aspects of the present invention will be more fully understood upon a review of the following description of the preferred embodiment when considered in conjunction with the drawings.

DESCRIPTION OF THE PREFERRED EMBODIMENT

Figure 1:
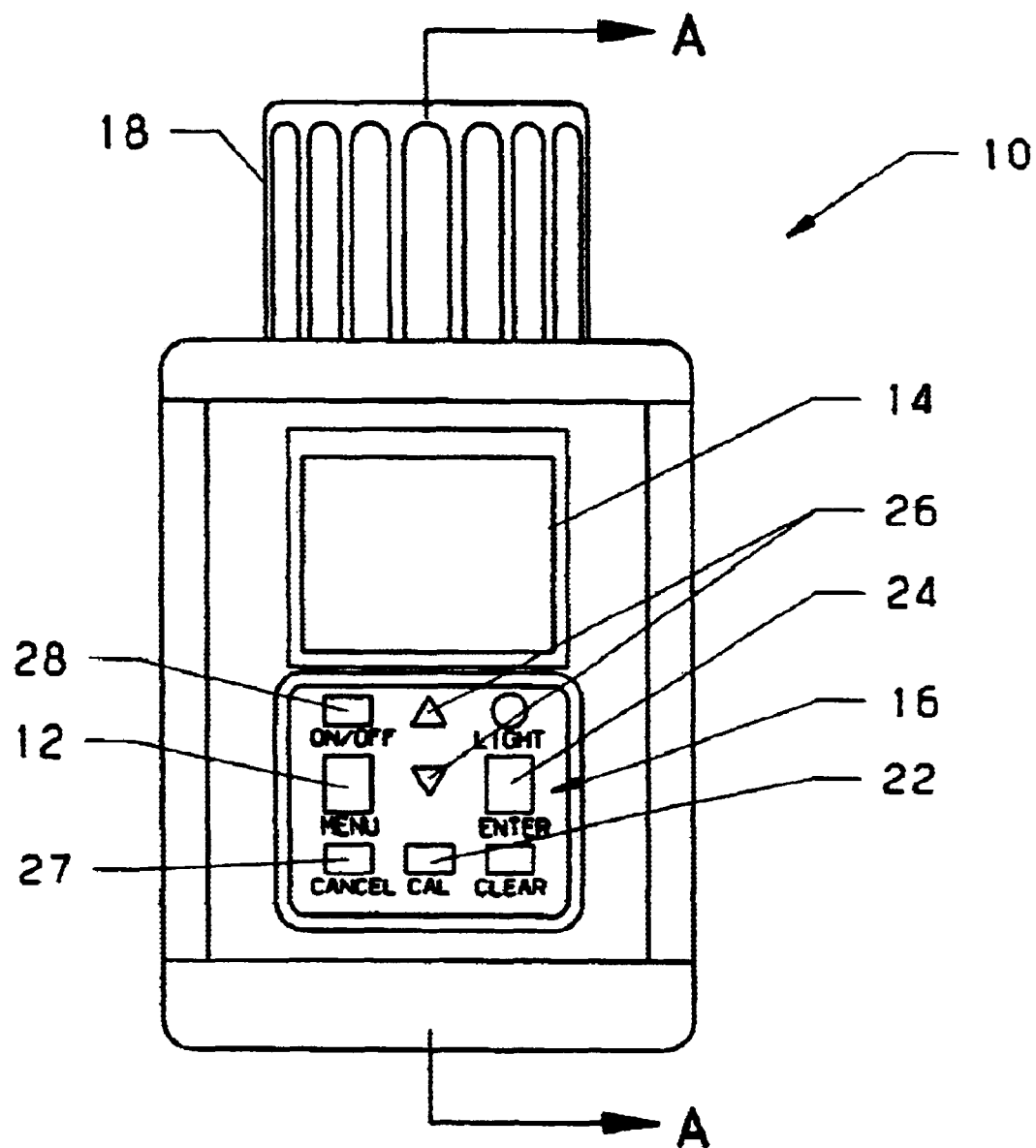
FIG. 1. is a front view of the portable grain moisture meter of the present invention.
Figure 2:
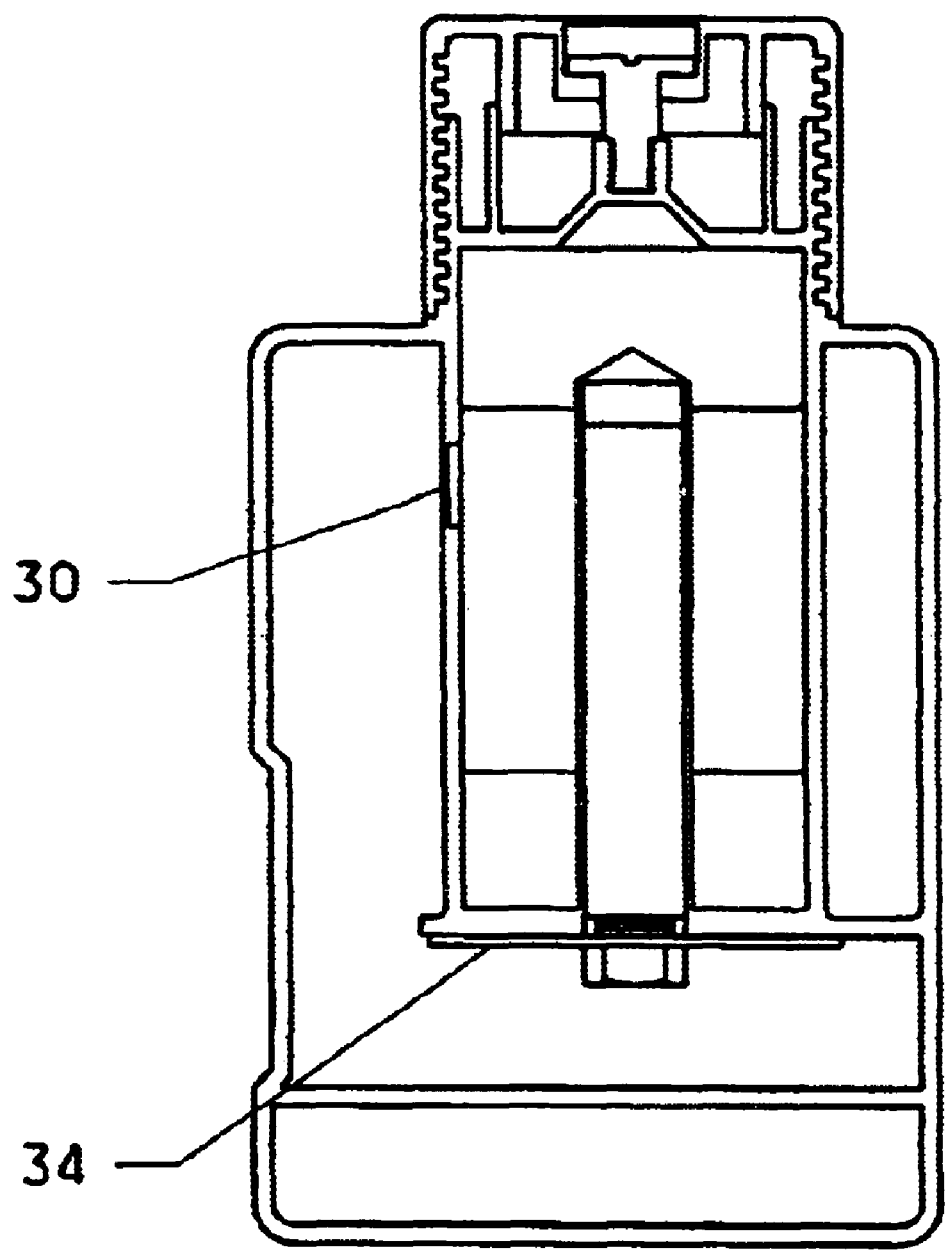
FIG. 2. is cut-away view of the FIG. 1 meter taken along section A—A.
Figure 3:
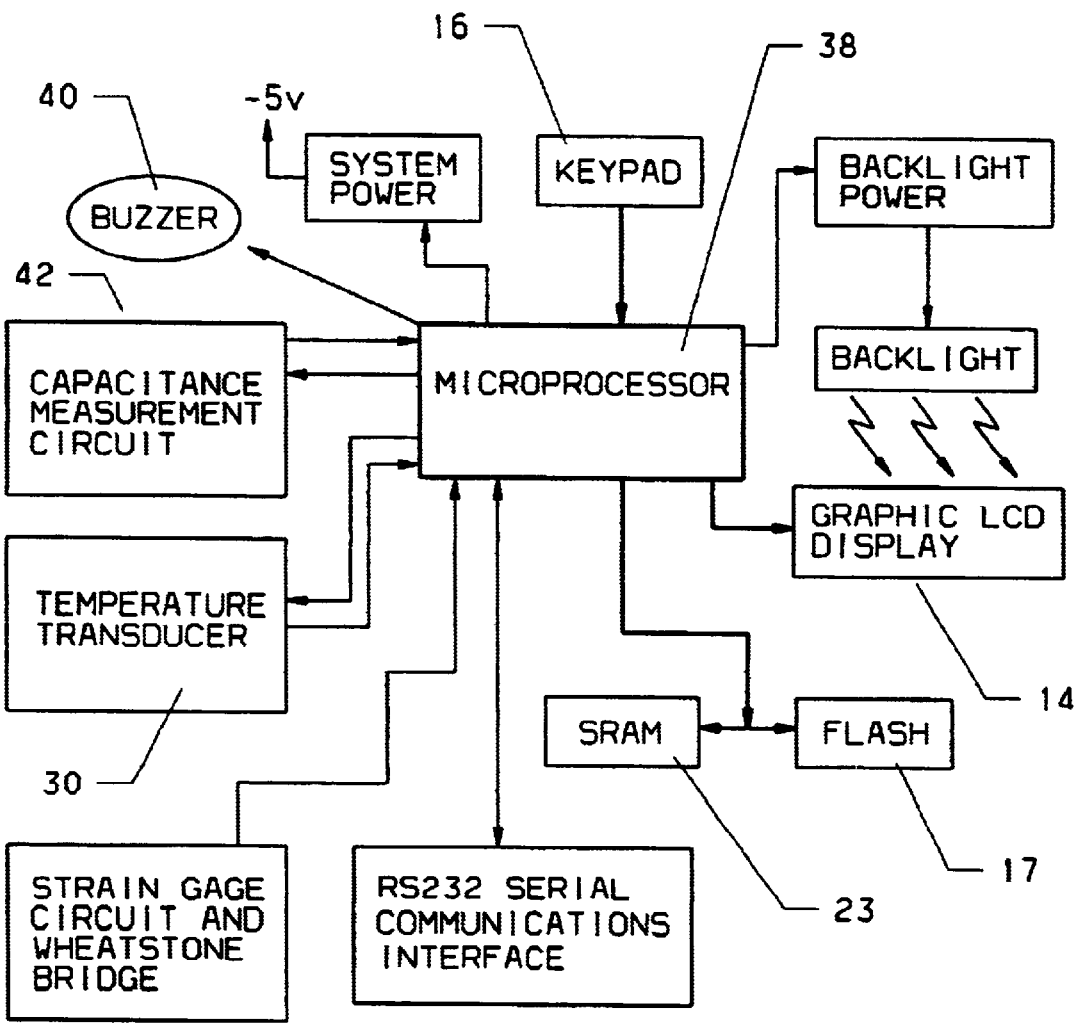
FIG. 3. is a block diagram electronic circuitry used by the FIG. 1. meter.
Figure 4:
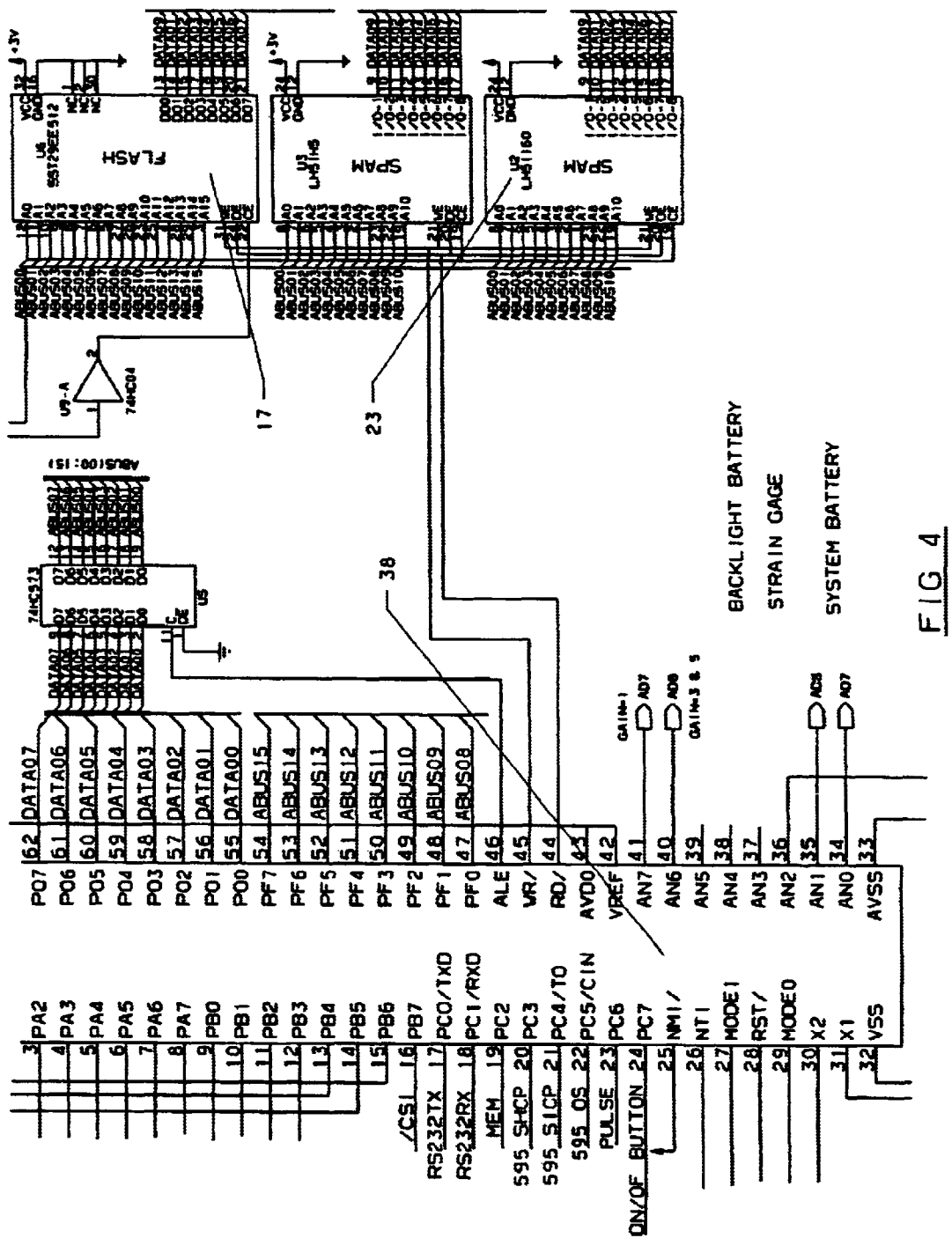
FIG. 4. is a schematic of the circuitry for the memory where the lookup tables are stored and the microprocessor of the FIG. 1 tester.

Turning now to the drawing where the showings are intended to depict a preferred embodiment of the present invention but not limit the invention thereto, FIGS. 1–4 show a portable grain moisture meter (10) having a graphic LCD display (14) and a keypad (16) for user inputs and a flash memory (17) where the calibration lookup tables and user offsets are stored.

The moisture meter (10) is a capacitive type grain moisture meter, which uses a constant grain volume as the capacitance dielectric material. The signal attenuation across the grain varies with moisture content of the dielectric and therefore is proportional to the grain moisture. Such a device is generally described in prior art U.S. Pat. Nos. 3,761,810 and 3,781,673 the contents of which are incorporated by reference herein and the reader is referred thereto for further details of the general structure and operation of such devices.

To initiate a moisture measurement, the user must first turn the tester (10) on by depressing an on/off push button (28) located on the keypad (16). The user must now determine if the tester (10) is selected to match the commercial tester he wants to compare it to. To select the programmed calibration curve for the commercial tester that the user wants to compare, the user must now press the menu push button (12). The microprocessor (38) will now send a signal to the LCD (14) to display a list of menu options. The user must then use use/down push buttons (26), select the commercial tester option and press an enter push button (24). The microprocessor (38) will now send a signal to the LCD (14) to display the list of commercial tester calibrations available in the tester (10). The user must then use the up/down push button (26), select the commercial tester and press the enter push button (24). The microprocessor (38) now stores the selected commercial tester selection in a flash (17) to be used later for testing. The user now presses the cancel push button (27) and the microprocessor (38) sends a signal to the LCD (1) to display the current grain commodity that is selected to be tested. The user can now use the up/down push buttons (26) to change the current rain hat will be used before taking the test.

The user now fills the tester (10) with the grain commodity to be tested and places a cap (18) on the tester. The user now screws down the cap (18). The microprocessor (38) reads the signal from a strain gauge (34) to determine when to initiate the dielectric test of the commodity. This is done by comparing the measured strain guage (34) signal to a preset signal in the microprocessor (38) indicative of an optimum grain compaction or pressure in the test cell. When the measured signal reaches the preset signal testing is initiated by the microprocessor (38). When the grain is optimally compacted and is ready to be tested, the microprocessor (38) stores in SRAM (23) the measurement of the dielectric of the grain from circuit (42) and also the temperature of the grain from temperature transducer (30). Then the microprocessor (38) sends a signal to the LCD (14) to display TESTING and also a signal to a buzzer (40) to indicate to the user to stop screwing down the cap (18) since the test has been initiated and further compaction is not necessary. The microprocessor (38) now uses the selected grain commodity and commercial tester to decided which lookup table in the flash (17) to use to determine the moisture of the grain. The lookup is a multiple point lookup table each point consisting of a dielectric value, a corresponding moisture value and a moisture offset value. The microprocessor (38) now takes the dielectric value in SRAM (23), finds the corresponding dielectric value in the lookup table in flash (17) and uses the corresponding moisture value then adding or subtracting the corresponding moisture offset value to the moisture value of the point to determine what the moisture of the commodity is.

The microprocessor (38) now applies temperature compensation to the moisture value and stores the moisture value in SRAM (23). The microprocessor (38) now sends a signal to the LCD (14) to display the moisture value stored in the SRAM (23) to the LCD (14). The user can now press the cancel push button (26) to perform another test or press the cal push button (22). If the user presses the cal push button (22) the microprocessor (38) sends a signal to the LCD (14) to display a menu to allow the user to either reset or adjust the calibration of the selected commodity and commercial tester.

If the user selects the reset option, using the up/down arrow push o buttons (26), and then presses the enter push button (24) the microprocessor (38) then sends a signal to the LCD (14) to display a confirmation that they wish to reset the calibration. If the user, using the up/down push buttons (26), selects YES and press the enter push button (24) The microprocessor (8) will reset all the moisture offset points in the selected lookup table to 0 percent in the flash (17) where the lookup tables are stored. The microprocessor (38) now sends a signal to the LCD (14) to display the screen for performing another test.

If the user selected the adjust option instead of the reset calibration the microprocessor (38) will send a signal to the LCD (14) to display a screen that will allow the user to adjust the moisture value that he has just tested. The LCD (14) displays both the current moisture value tested and a commercial tester moisture. The user, by pressing the up/down push buttons (26), can adjust the commercial tester moisture value on the LCD (14) to match the actual commercial testers results. The LCD (14) will also displays the percentage adjusted based on the difference between the commercial tester moisture value and the testers current moisture value. The microprocessor (38) will then store the adjusted percentage value in SRAM (23). The user now presses the enter push button (24) and the microprocessor (38) then lookup the current tested moisture value stored in SRAM (23) in the lookup table in flash (17) and then stores in the corresponding moisture offset point in flash (17) the percentage adjusted stored in SRAM (23) to apply a new offset for the given tested moisture point. This is important be use the tester only applies the offset to the specific moisture point that was tested rather that the the entire lookup table used for calibration.

The microprocessor (38) now checks the current lookup table in the flash (17) to determine, if after the calibration adjustments, the adjacent moisture point of the table in flash (17) needs to be adjusted. The microprocessor (38) checks from the beginning of the current lookup table in flash (17) to the end to ensure that all the moisture points, when applying their corresponding moisture offset are in ascending order. If the current lookup table in flash (17) is not in an ascending order the microprocessor (38) will adjust the necessary moisture offsets in flash (17) to correct the current lookup table in flash (17).

Next, the microprocessor sends a signal to the LCD (14) to display the option of viewing a graph of the current calibration curve. If the user selects no using the up/down push buttons (26) and presses the enter push button (24) the microprocessor (38) will now send a signal to the LCD (14) to display the option to perform another test. If the user selects yes using the up/down push buttons (26) and presses the enter push button (24) the microprocessor will end a signal to the LCD (14) to display a graphical representation of the current lookup table in flash (17) which is the calibration curve for the currently selected commodity. The user can now press the enter push button (24) and the microprocessor (38) sends a signal to the LCD (14) to display the options to perform another test.

Certain modifications and additions to the present portable meter's description have been deleted herein for the sake of conciseness and readability but are fully intended to be within the scope of the following claims. As an example, details of the circuitry for making the dielectric and temperature measurements are well known and are not belabored in this specification.

We claim:

1. A portable grain moisture meter comprising:
   a readout for displaying various menus indicative of various functions available to a user of the meter;
   a keyboard for actuating selections from said menus displayed on said readout;
   a memory located in the meter having a multi point look up table stored therein;
   a series of calibrated commercial tester measurement ranges stored in said memory and other tester information stored in said look up table of said memory; and
   a microprocessor for displaying one menu indicative of said series of calibrated commercial tester measurement ranges located in said memory and being responsive to a keyboard actuation to select one of said series for use by the meter in performing a moisture measurement.

2. A moisture meter as set forth in claim 1 including a series of various grain commodities located in said memory and being responsive to a keyboard actuation to use in making an actual moisture measurement.

3. A moisture meter as set forth in claim 2 including means for manually offsetting said actual moisture measurement to conform said measurement to a particular commercial tester measurement.

4. A moisture meter as set forth in claim 3 including a strain guage located in a test cell of the meter and an automatic moisture test initiator based on sensing a particular test cell compression as measured by said strain guage.

5. A moisture meter as set forth in claim 1 wherein said lookup table includes multiple points consisting of dialectric values with corresponding moisture values and moisture offset values for various grains and commercial tester.

6. A method conforming the moisture measurements taken by a portable grain moisture meter to any of a plurality of differing manufacturers differently calibrate commercial moisture testers found in grain purchasing facilities comprising the steps of:
   providing a calibrated measurement range for each of the plurality of differing manufacturers differently calibrated commercial testers in the memory of the portable moisture meter;
   selecting one of said plurality of commercial testers which will be used by the grain elevator where the operator will sell his grain and inputting its calibrated measurement range into the testing circuit of the portable meter; and
   making measurements for optimum moisture content in the grain.

7. A method of conforming the moisture measurements taken by a portable grain moisture meter to any of a plurality of differing manufacturers commercial moisture testers as set forth in claim 6 including the step of offsetting any differences between the moisture measurement taken by the portable meter and the measurement of the particular commercial tester.

8. A portable grain moisture meter comprising:
   a readout for displaying various menus indicative of various functions available to a user of the meter;

a keyboard for actuating selections from said menus displayed on said readout;

a memory located in the meter;

a series of commercial tester measurement ranges stored in said memory;

a microprocessor for displaying one menu indicative of said series of calibrated commercial tester measurement ranges located in said memory and being responsive to a keyboard actuation to select one of said series for use by the meter in performing a moisture measurement;

said memory including a series of various grain commodities being responsive to a keyboard actuation to use in making an actual moisture measurement;

means for manually offsetting said actual moisture measurement to conform said measurement to a particular commercial tester measurement; and including a strain guage located in a test cell of the meter and an automatic moisture test initiator or based on sensing a particular test cell compression as measured by said strain guage.

* * * * *